United States Patent
Zhang

(10) Patent No.: US 9,353,062 B2
(45) Date of Patent: May 31, 2016

(54) SUBSTITUTED QUINOLINES AS BRUTON'S TYROSINE KINASES INHIBITORS

(71) Applicant: HangzhouDeRenYuCheng Biotechnology Ltd, Hangzhou (CN)

(72) Inventor: Dawei Zhang, Thousand Oaks, CA (US)

(73) Assignee: HangzhouDeRenYuCheng Biotechnology Ltd, Hangzhou (CN)

( * ) Notice: Subject to any disclaimer, the term of this patent is extended or adjusted under 35 U.S.C. 154(b) by 0 days.

(21) Appl. No.: 14/390,771

(22) PCT Filed: Apr. 3, 2013

(86) PCT No.: PCT/US2013/035176
§ 371 (c)(1),
(2) Date: Oct. 3, 2014

(87) PCT Pub. No.: WO2013/152135
PCT Pub. Date: Oct. 10, 2013

(65) Prior Publication Data
US 2015/0057312 A1  Feb. 26, 2015

Related U.S. Application Data

(60) Provisional application No. 61/686,321, filed on Apr. 4, 2012.

(51) Int. Cl.
| | | |
|---|---|---|
| C07D 215/44 | (2006.01) |
| A61K 31/4706 | (2006.01) |
| C07D 215/48 | (2006.01) |
| A61K 45/06 | (2006.01) |
| C07D 215/54 | (2006.01) |
| C07D 401/12 | (2006.01) |
| C07D 405/12 | (2006.01) |

(52) U.S. Cl.
CPC .......... *C07D 215/44* (2013.01); *A61K 31/4706* (2013.01); *A61K 45/06* (2013.01); *C07D 215/48* (2013.01); *C07D 215/54* (2013.01); *C07D 401/12* (2013.01); *C07D 405/12* (2013.01)

(58) Field of Classification Search
CPC ............... C07D 215/48; C07D 215/44; A61K 31/4706; A61K 45/06
USPC .......................................... 546/160; 514/313
See application file for complete search history.

(56) References Cited

U.S. PATENT DOCUMENTS

| | | | |
|---|---|---|---|
| 6,002,008 A * | 12/1999 | Wissner et al. ............... 546/160 |
| 7,585,869 B2 * | 9/2009 | Bhattacharya et al. .. 514/266.22 |
| 2004/0242604 A1 * | 12/2004 | Bhattacharya et al. .... 514/266.4 |
| 2006/0270670 A1 | 11/2006 | Chew et al. |

OTHER PUBLICATIONS

Hwei-Ru Tsou et al, 2005, pp. 1107-1131, Optimization of 6,7-Disubstituted-4-(arylamino)quinoline-3-carbonitriles as Orally Active, Irreversible Inhibitors of Human Epidermal Growth Factor Receptor-2 Kinase Activity.*

* cited by examiner

*Primary Examiner* — Rita Desai
(74) *Attorney, Agent, or Firm* — Feng Tian

(57) ABSTRACT

The present invention is directed to novel quinolines, their derivatives, pharmaceutically acceptable salts, solvates and hydrates thereof. The compounds and compositions of the present invention have protein kinases inhibitory activities and are useful for the treatment of protein kinases mediated diseases and conditions. The disclosed substituted quinolines include Bruton's tyrosine kinase (Btk) inhibitors.

8 Claims, No Drawings

SUBSTITUTED QUINOLINES AS BRUTON'S TYROSINE KINASES INHIBITORS

CROSS REFERENCE TO RELATED APPLICATION

The application is a 35 U.S.C. §371 national stage filing of International Patent Application PCT/US2013/035176 (published as WO 2013/152135 A1), filed Apr. 3, 2013, which is entitled to priority pursuant to 35 U.S.C. §119(e) to U.S. Provisional Application No. 61/686,321, filed Apr. 4, 2012. The entire disclosures of the afore-mentioned patents are hereby incorporated by reference in their entirety. This invention claims the benefit of U.S. Provisional Patent Application No. 61/686,321 filed on Apr. 4, 2012, which is incorporated herein by reference in its entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Due to their activity in numerous cellular processes, protein kinases have emerged as important therapeutic targets.

Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

Bruton's tyrosine kinase (Btk) plays a key role in promoting B cell proliferation and survival through participation in the B cell receptor (BCR) signaling pathway and represents a promising new drug target. Targeted therapies that suppress BCR signaling have emerged as promising agents in the treatment of several B cell malignancies. To this end, attempts have been made to identify small molecules which act as Btk inhibitors. For example, U.S. Pat. No. 7,982,036 describes 4,6-disubstituted pyrimidine compounds as useful kinase inhibitors targeting the Tec kinase family. The disclosed compounds include Btk inhibitors. Another class of Btk inhibitors has been disclosed in U.S. Pat. No. 8,088,781.

Thus, the compounds that can inhibit protein kinases such as Bruton's tyrosine kinase (Btk) activity are highly desired.

SUMMARY OF THE INVENTION

In some embodiments of the present invention, there are provided compounds of Formula I:

I or a pharmaceutically acceptable salt, solvate or a prodrug or a stereoisomer or a tautomer or a metabolite thereof, wherein
$R_1$ is selected from
a) Hydrogen or —$(CH_2)_m$—$NR_5R_6$;
b) —$(CH_2)_m$-Het; Het is morpholine, piperidine, piperazine, piperazine-N($C_1$-$C_3$ alkyl), pyrrolidine, each optionally substituted by alkyl, halo, OH, $NH_2$, NH($C_1$-$C_3$ alkyl) or N($C_1$-$C_3$ alkyl)$_2$;
$R_2$ is selected from
a) Hydrogen, $C_1$-$C_6$ alkyl, F, Cl or $CF_3$;
b) —$OR_7$;
$R_3$ and $R_4$ are independently selected from hydrogen, $C_1$-$C_6$ alkyl, halo, CN, or $CF_3$; with the proviso that when $R_3$ is chloro, then $R_4$ is $C_1$-$C_6$ alkyl, halo, CN, or $CF_3$;
$R_5$ and $R_6$ are independently selected from hydrogen, or $C_1$-$C_6$ alkyl;
$R_7$ is selected from
a) $C_1$-$C_6$ straight or branched alkyl, optionally substituted by one or more halogens or $C_1$-$C_6$ alkoxy.
b) Tetrahydrofuran-3-yl;
c) —$(CH_2)_m$-morpholine, —$(CH_2)_m$-piperidine, —$(CH_2)_m$-piperazine-N($C_1$-$C_3$ alkyl);
m is 1-3.

DETAILED DESCRIPTION OF THE INVENTION

In some embodiments of the present invention, there are provided compounds of Formula I:

I or a pharmaceutically acceptable salt, solvate or a prodrug or a stereoisomer or a tautomer or a metabolite thereof, wherein
$R_1$ is selected from
c) Hydrogen or —$(CH_2)_m$—$NR_5R_6$;
d) —$(CH_2)_m$-Het; Het is morpholine, piperidine, piperazine, piperazine-N($C_1$-$C_3$ alkyl), pyrrolidine, each optionally substituted by alkyl, halo, OH, $NH_2$, NH($C_1$-$C_3$ alkyl) or N($C_1$-$C_3$ alkyl)$_2$;
$R_2$ is selected from
c) Hydrogen, $C_1$-$C_6$ alkyl, F, Cl or $CF_3$;
d) —$OR_7$;
$R_3$ and $R_4$ are independently selected from hydrogen, $C_1$-$C_6$ alkyl, halo, CN, or $CF_3$; with the proviso that when $R_3$ is chloro, then $R_4$ is $C_1$-$C_6$ alkyl, halo, CN, or $CF_3$;

R₅ and R₆ are independently selected from hydrogen, or $C_1$-$C_6$ alkyl;

R₇ is selected from d) $C_1$-$C_6$ straight or branched alkyl, optionally substituted by one or more halogens or $C_1$-$C_6$ alkoxy.

e) Tetrahydrofuran-3-yl;

f) —(CH₂)$_m$-morpholine, —(CH₂)$_m$-piperidine, —(CH₂)$_m$-piperazine-N($C_1$-$C_3$ alkyl); m is 1-3.

In certain embodiments, R₁ is hydrogen. In some embodiments, R₁ is N,N-dimethylaminomethyl. In other embodiments, R₂ is hydrogen. In some embodiments, R₂ is chlorine. In other embodiments R₃ is hydrogen. In certain embodiments, R₃ is chlorine. In other embodiments, R₄ is hydrogen. In certain embodiments, R₃ or R₄ is fluorine. In some embodiments, both R₅ and R₆ are methyl. In some embodiments, R₇ is methyl or ethyl. In other embodiments, R₇ is tetrahydrofuran-3-yl. In other embodiments, the compound of Formula I is in the form of pharmaceutically acceptable salt. In some embodiments, the compound of Formula I is in the form of a solvate. In other embodiments, the compound of Formula I is in the form of a metabolite. In other embodiments, the compound of Formula I is in the form of a prodrug. In some embodiments, the compound of Formula I is a stereoisomer. In other embodiments, the compound of Formula I is a tautomer. In another embodiment, the deuterium enrichment in compounds of Formula I is at least about 1%.

In certain embodiments, there are provided compounds without limitation selected from the group consisting of:

N-(3-cyano-4-((4-phenoxyphenyl)amino)quinolin-6-yl)acrylamide;

N-(4-((4-(3-chlorophenoxy)phenyl)amino)-3-cyanoquinolin-6-yl)acrylamide;

N-(3-cyano-7-ethoxy-4-((3-fluoro-4-phenoxyphenyl)amino)quinolin-6-yl)acrylamide;

N-(3-cyano-7-methoxy-4-((4-phenoxyphenyl)amino)quinolin-6-yl)acrylamide;

N-(3-cyano-7-ethoxy-4-((4-phenoxyphenyl)amino)quinolin-6-yl)acrylamide;

N-(4-((3-chloro-4-(4-fluorophenoxy)phenyl)amino)-3-cyano-7-ethoxyquinolin-6-yl)acrylamide;

N-(3-cyano-7-ethoxy-4-((4-(3-(trifluoromethyl)phenoxy)phenyl)amino)quinolin-6-yl)acrylamide;

N-(4-((3-chloro-4-(pyridin-2-ylmethoxy)phenyl)amino)-3-cyano-7-ethoxyquinolin-6-yl)acrylamide;

N-(4-((3-chloro-4-((3-fluorobenzyl)oxy)phenyl)amino)-3-cyano-7-ethoxyquinolin-6-yl)acrylamide;

N-(3-cyano-7-ethoxy-4-((4-(pyridin-2-ylmethoxy)phenyl)amino)quinolin-6-yl)acrylamide;

N-(3-cyano-7-ethoxy-4-((4-((3-fluorobenzyl)oxy)phenyl)amino)quinolin-6-yl)acrylamide;

N-(4-((3-chloro-4-(pyridin-2-ylmethoxy)phenyl)amino)-3-cyanoquinolin-6-yl)acrylamide;

N-(3-cyano-4-((3-fluoro-4-((3-fluorobenzyl)oxy)phenyl)amino)quinolin-6-yl)acrylamide;

N-(3-cyano-4-((4-phenoxyphenyl)amino)-7-((tetrahydrofuran-3-yl)oxy)quinolin-6-yl)acrylamide;

(R)—N-(3-cyano-4-((4-phenoxyphenyl)amino)-7-((tetrahydrofuran-3-yl)oxy)quinolin-6-yl)acrylamide;

N-(3-cyano-4-((4-(3-(trifluoromethyl)phenoxy)phenyl)amino)quinolin-6-yl)acrylamide;

N-(3-cyano-7-ethoxy-4-((4-(4-fluorophenoxy)phenyl)amino)quinolin-6-yl)acrylamide;

(E)-N-(3-cyano-7-ethoxy-4-((4-phenoxyphenyl)amino)quinolin-6-yl)-4-(piperidin-1-yl)but-2-enamide;

(R,E)-N-(3-cyano-4-((4-phenoxyphenyl)amino)-7-((tetrahydrofuran-3-yl)oxy)quinolin-6-yl)-4-(dimethylamino)but-2-enamide;

(E)-N-(3-cyano-7-ethoxy-4-((4-phenoxyphenyl)amino)quinolin-6-yl)-4-(dimethylamino)but-2-enamide;

(E)-N-(3-cyano-7-ethoxy-4-((3-fluoro-4-phenoxyphenyl)amino)quinolin-6-yl)-4-(piperidin-1-yl)but-2-enamide;

(E)-N-(3-cyano-4-((4-phenoxyphenyl)amino)-7-((tetrahydrofuran-3-yl)oxy)quinolin-6-yl)-4-(dimethylamino)but-2-enamide;

(E)-N-(3-cyano-4-((4-phenoxyphenyl)amino)quinolin-6-yl)-4-(piperidin-1-yl)but-2-enamide;

(E)-N-(3-cyano-4-((4-phenoxyphenyl)amino)quinolin-6-yl)-4-(dimethylamino)but-2-enamide;

(E)-N-(3-cyano-7-ethoxy-4-(4-(pyridin-2-yloxy)phenyl)amino)quinolin-6-yl)-4-(dimethylamino)but-2-enamide;

(E)-N-(3-cyano-7-ethoxy-4-(4-(4-fluorophenoxy)phenyl)amino)quinolin-6-yl)-4-(dimethylamino)but-2-enamide;

(E)-N-(4-(4-(3-chlorophenoxy)-3-fluorophenyl)amino)-3-cyanoquinolin-6-yl)-4-(dimethylamino)but-2-enamide;

(E)-N-(4-((3-chloro-4-(3-fluorophenoxy)phenyl)amino)-3-cyanoquinolin-6-yl)-4-(dimethylamino)but-2-enamide;

(E)-N-(4-((3-chloro-4-(3-fluorophenoxy)phenyl)amino)-3-cyano-7-ethoxyquinolin-6-yl)-4-(dimethylamino)but-2-enamide;

(E)-N-(4-((3-chloro-4-(3-(trifluoromethyl)phenoxy)phenyl)amino)-3-cyano-7-ethoxyquinolin-6-yl)-4-(dimethylamino)but-2-enamide;

(E)-N-(3-cyano-7-ethoxy-4-((3-fluoro-4-phenoxyphenyl)amino)quinolin-6-yl)-4-(dimethylamino)but-2-enamide;

(E)-N-(3-cyano-7-ethoxy-4-((3-fluoro-4-(4-fluorophenoxy)phenyl)amino)quinolin-6-yl)-4-(dimethylamino)but-2-enamide;

(E)-N-(3-cyano-4-((3-fluoro-4-phenoxyphenyl)amino)-7-(2-methoxyethoxy)quinolin-6-yl)-4-(dimethylamino)but-2-enamide;

(E)-N-(3-cyano-4-((3-fluoro-4-phenoxyphenyl)amino)-7-(2-morpholinoethoxy)quinolin-6-yl)-4-(dimethylamino)but-2-enamide;

(E)-N-(4-((3-chloro-4-((3-fluorobenzyl)oxy)phenyl)amino)-3-cyano-7-ethoxyquinolin-6-yl)-4-(dimethylamino)but-2-enamide;

(E)-N-(3-cyano-7-ethoxy-4-((4-(pyridin-2-ylmethoxy)phenyl)amino)quinolin-6-yl)-4-(dimethylamino)but-2-enamide;

(E)-N-(3-cyano-7-ethoxy-4-((4-((3-fluorobenzyl)oxy)phenyl)amino)quinolin-6-yl)-4-(dimethylamino)but-2-enamide;

(E)-N-(4-((3-chloro-4-(pyridin-2-ylmethoxy)phenyl)amino)-3-cyanoquinolin-6-yl)-4-(dimethylamino)but-2-enamide;

(E)-N-(4-((3-chloro-4-((3-fluorobenzyl)oxy)phenyl)amino)-3-cyanoquinolin-6-yl)-4-(dimethylamino)but-2-enamide;

(E)-N-(3-cyano-4-((4-(pyridin-2-ylmethoxy)phenyl)amino)quinolin-6-yl)-4-(dimethylamino)but-2-enamide;

(E)-N-(3-cyano-4-((3-fluoro-4-((3-fluorobenzyl)oxy)phenyl)amino)quinolin-6-yl)-4-(dimethylamino)but-2-enamide, and the like, or a pharmaceutically acceptable salt, solvate, or a prodrug, or a metabolite thereof. In some embodiments, there are provided pharmaceutical compositions comprising a compound of formula I and a pharmaceutically acceptable carrier. In certain embodiments, the compositions are for the treatment of a disease regulated by a protein kinase. In certain embodiments, the compositions are for or the treatment of a hyper-proliferative disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present invention provides methods for regulating the kinase signaling transduction, said methods comprising administrating to a mammalian subject a therapeutically effective amount of a compound of Formula I.

In other embodiments, there are provided herein methods for treating or preventing a Bruton's tyrosine kinase (Btk) mediated disorder, said method comprising administrating to a mammalian subject a therapeutically effective amount of a compound of Formula I.

In yet another aspect, there are provided herein methods for inhibiting human epidermal growth factor receptor (HER) kinases, said methods comprising administrating to a mammalian subject a therapeutically effective amount of a compound of Formulas I.

In other embodiments, there are provided herein methods for treating neoplasia, said methods comprising administrating to a mammalian subject in need of treatment, a therapeutically effective amount of a compound of Formulas I. In certain embodiments, the neoplasia is selected from B cell malignancies, liver cancer, skin cancer, leukemia, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer and prostate cancer. In certain embodiments, chronic lymphocytic leukemia, mantle cell lymphoma, diffuse large B-cell lymphoma, and multiple myeloma, breast cancer or the lung cancer. In some embodiments, the methods further comprise administering one or more anti-cancer agents.

The following definitions should assist in understanding the invention described herein.

The term "alkyl" is intended to include straight, branched, and cyclic hydrocarbon groups, which contain only single carbon-carbon bonds and which may be unsubstituted or optionally substituted with one or more functional groups. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. The chain length of an alkyl group is from 1 to 6 carbon atoms. $C_1$-$C_3$ alkyl is intended to include $C_1$, $C_2$ and $C_3$ alkyl groups. $C_1$-$C_6$ alkyl is intended to include $C_1$, $C_2$, $C_3$, $C_4$, $C_5$ and $C_6$ alkyl groups. The term "substituted" or "optionally substituted," when describing an alkyl group, is intended to include one or more substituents on the alkyl group. The substituents are independently selected from halogen, hydroxyl, and $C_1$-$C_6$ alkoxy. Illustrative substituted alkyl group include, but are not limited to, fluoromethyl, difluoromethyl, trifluoromethyl, hydroxymethyl, methoxymethyl, 2-fluoroethyl, 2-methoxyethyl, etc. The term "alkoxy" refers to —O—R wherein R is an alkyl group. $C_1$-$C_6$ alkoxy is intended to include $C_1$-$C_6$ alkyl groups, wherein $C_1$-$C_6$ alkyl is defined above.

Halogen means fluorine, chlorine, bromine, and iodine. Halo means fluoro, chloro, bromo, and iodo.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}C$. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "isotopic enrichment factor" as used herein means the ratio between the isotopic abundance and the natural abundance of a specified isotope.

The term "comprising" is meant to be open-ended, including the indicated component(s), but not excluding other elements.

The term "pharmaceutically acceptable" when used with reference to a compound of Formulas I is intended to refer to a form of the compound that is safe for administration to a subject. For example, a free base, a salt form, a solvate, a hydrate, a prodrug or derivative form of a compound of Formula I, which has been approved for mammalian use, via oral ingestion or any other route of administration, by a governing authority or regulatory agency, such as the Food and Drug Administration (FDA) of the United States, is pharmaceutically acceptable.

Included in the compounds of Formula I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug, which is pharmaceutically acceptable.

In some embodiments, the compound(s) of Formula I are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973), T. W. Greene and P. G. M. Wuts, *Protective Groups in Organic Synthesis*, Wiley, 3$^{rd}$ edition, John Wiley and Sons (1999), E. Gross and J. Meienhofer, *The Peptides*, Volume 3, Academic Press, London and New York (1981), H. Weyl, *Methoden der Organischen Chemie (Methods of Organic Chemistry)*, 4th edition, Volume 15/1, Georg Thieme Verlag, Stuttgart (1974), H.-D. Jakubke and H. Jescheit, Aminosäuren, *Peptide, Proteine (Amino Acids, Peptides, Proteins)*, Verlag Chemie, Weinheim, Deerfield Beach, and Basel (1982), and Jochen Lehmann, *Chemie der Kohlenhydrate: Monosaccharide and Derivate (Chemistry of Carbohydrates: Monosaccharides and Derivatives)*, Georg Thieme Verlag, Stuttgart (1974).

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In selected embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

When synthesizing a compound of formulas I according to a desired procedure, the steps in some embodiment are performed in an order suitable to prepare the compound, including a procedure described herein or by an alternate order of steps described herein, and in one embodiment, be preceded, or followed, by additional protection/deprotection steps as necessary. In certain embodiment, the procedures further use appropriate reaction conditions, including inert solvents, additional reagents, such as bases (e.g., LDA, DIEA, pyridine, $K_2CO_3$, and the like), catalysts, and salt forms of the above. The intermediates in some embodiments are isolated or carried on in situ, with or without purification. Purification methods are known in the art and include, for example, crystallization, chromatography (liquid and gas phase, and the like), extraction, distillation, trituration, reverse phase HPLC and the like. Reaction conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art, and include, for example, those such as those described in R. Larock, *Comprehensive Organic Transformations*, VCH Publishers (1989); T. W. Greene and P. G. M. Wuts, *Protective Groups in Organic Synthesis,* 3rd edition, John Wiley and Sons (1999); L. Fieser and M. Fieser, *Fieser and Fieser's Reagents for Organic Synthesis*, John Wiley and Sons (1994); A. Katritzky and A. Pozharski, *Handbook of Heterocyclic Chemistry,* 2nd edition (2001); M. Bodanszky, A. Bodanszky, *The Practice of Peptide Synthesis*, Springer-Verlag, Berlin Heidelberg (1984); J. Seyden-Penne, *Reductions by the Alumino-and Borohydrides in Organic Synthesis,* 2nd edition, Wiley-VCH, (1997); and L. Paquette, editor, *Encyclopedia of Reagents for Organic Synthesis*, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

These detailed descriptions are presented for illustrative purposes only and are not intended as a restriction on the scope of the invention.

Biological Assays:

As stated hereinbefore, the compounds defined in the present invention possess anti-proliferation activity. These properties may be assesses, for example, using one or more of the procedures set out below:

An in vitro assay which determines the ability of a test compound to inhibit Btk.

a) Method A conducts the kinase assay with the following condition and procedure: Reagent: Base Reaction Buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO.

Reaction Procedure:
1. Prepare indicated substrate in freshly prepared Base Reaction Buffer.
2. Deliver any required cofactors to the substrate solution obtained in step 1.
3. Deliver indicated kinase into the substrate solution prepared in step 2 and gently mix.
4. Deliver compounds in DMSO into the kinase reaction mixture prepared in step 3.
5. Deliver $^{33}$P-ATP (specific activity 0.01 μCi/μl final) into the reaction mixture prepared in step 4 to initiate the reaction.
6. Incubate kinase reaction for 120 min. at room temperature.
7. Reactions are spotted onto P81 ion exchange paper (Whatman #3698-915).
8. Washing filters extensively in 0.75% Phosphoric acid.

Compounds were tested in 10-dose IC50 mode with 3-fold serial dilution starting at 10 μM; Reactions were carried out at 10 μM ATP.

b) Method B conducts the kinase assay with the following condition and procedure: The assay was performed using Kinase-Glo Plus luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity.

The compounds were diluted in 10% DMSO and 5 μl of the dilution was added to a 50 μl reaction so that the final concentration of DMSO is 1% in all of reactions. All of the enzymatic reactions were conducted at 30° C. for 40 minutes. The 50 μl reaction mixture contains 40 mM Tris, pH 7.4, 10 mM $MgCl_2$, 0.1 mg/ml BSA, 1 mM DTT, 0.2 mg/ml substrate peptide, 10 μM ATP and BTK. After the enzymatic reaction, 50 μl of Kinase-Glo Plus Luminescence kinase assay solution (Promega) was added to each reaction and incubate the plate for 5 minutes at room temperature. Luminescence signal was measured using a BioTek Synergy 2 microplate reader. Btk activity assays were performed in duplicate at each concentration. The luminescence data were analyzed using the computer software, Graphpad Prism. The difference between luminescence intensities in the absence of Btk ($Lu_t$) and in the presence of Btk ($Lu_c$) was defined as 100% activity ($Lu_t$−$Lu_c$). Using luminescence signal (Lu) in the presence of the compound, % activity was calculated as % activity=$\{(Lu_t - Lu)/(Lu_t - Lu_c)\} \times 100\%$, where Lu=the luminescence intensity in the presence of the compound (all percent activities below zero were shown zero in the table). The values of % activity versus a series of compound concentrations were then plotted using non-linear regression analysis of Sigmoidal dose-response curve generated with the equation $Y=B+(T-B)/1+10^{((LogEC50-X)\times Hill\ Slope)}$, where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity. Compounds were tested in 10-dose IC50 mode with 3-fold serial dilution starting at 10 μM; Reactions were carried out at 10 μM ATP. Example 1 inhibited Btk activity with an $IC_{50}$ of 0.64 nM using method A.

The following Table 1 lists compounds representative of the invention and their inhibitory activity against Btk using method B.

TABLE 1

| Examples | Btk, $IC_{50}$ |
|---|---|
| 1 | <100 nM |
| 2 | <100 nM |

Btk Ramos Cellular Assay

Ramos cells were grown in suspension in T225 flasks, spun down, resuspended in 50 mL serum-free media and incubated for 1 hour. Compound was added to Ramos cells in serum free media to a final concentration of 1, 0.1, 0.01, or 0.001 μM. Ramos cells were incubated with compound for 1 hour, washed again and resuspended in 100 μL serum-free media. Cells were then stimulated with 1 μg of goat F(ab')2 Anti-Human IgM and incubated on ice for 10 minutes to activate B cell receptor signaling pathways. After 10 minutes, the cells were washed once with PBS and then lysed on ice with Invitrogen Cell Extraction buffer. Sixteen μg total protein from lysates was loaded on gels and blots were probed for phosphorylation of the BTK substrate PLC.gamma.2. Example 1 showed inhibition of BTK signaling in Ramos cells at $IC_{50}$ less than 100 nM.

Synthesis of Compounds

The compounds of Formula I were synthesized according to the procedures described in the following Schemes to those skilled in the art, wherein the substituents are as defined for Formulas I above, except where further noted. The synthetic methods described below are merely exemplary, and the compounds of the invention may also be synthesized by alternate routes as appreciated by persons of ordinary skill in the art. The reaction between literature known A and B under condition such as methyl sulfonic acid generated the intermediate C, which were acylated by D to afford compounds described in Formula I (Scheme 1).

Scheme 1

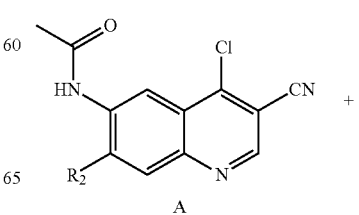

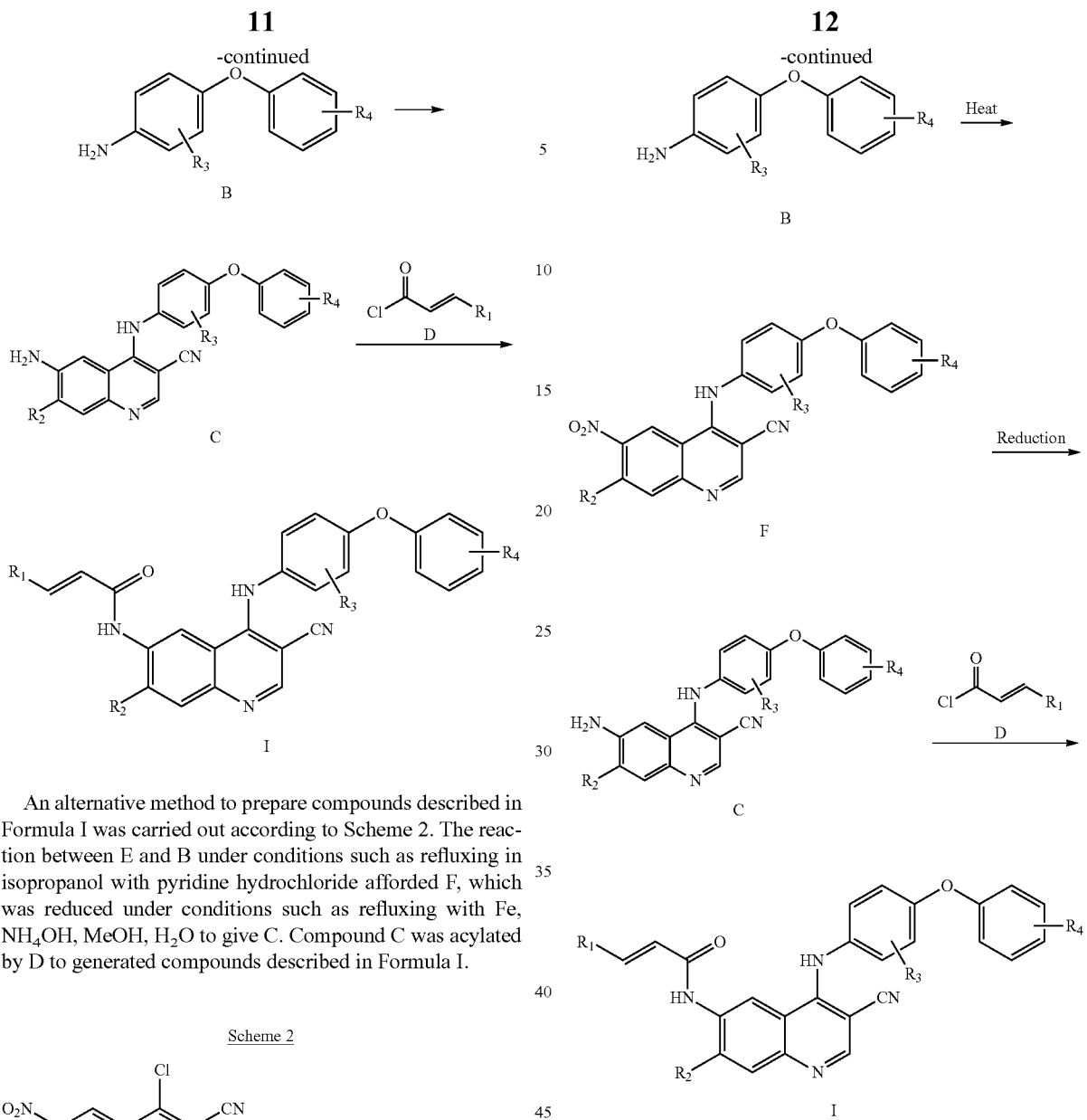

An alternative method to prepare compounds described in Formula I was carried out according to Scheme 2. The reaction between E and B under conditions such as refluxing in isopropanol with pyridine hydrochloride afforded F, which was reduced under conditions such as refluxing with Fe, NH$_4$OH, MeOH, H$_2$O to give C. Compound C was acylated by D to generated compounds described in Formula I.

Scheme 2

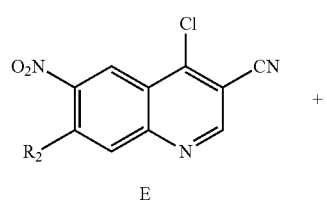

Still another alternative synthesis of compounds described in Formula I was described in Scheme 3. C was reacted with acyl chloride G, followed by replacement of halide with amine to afford I-1.

Scheme 3

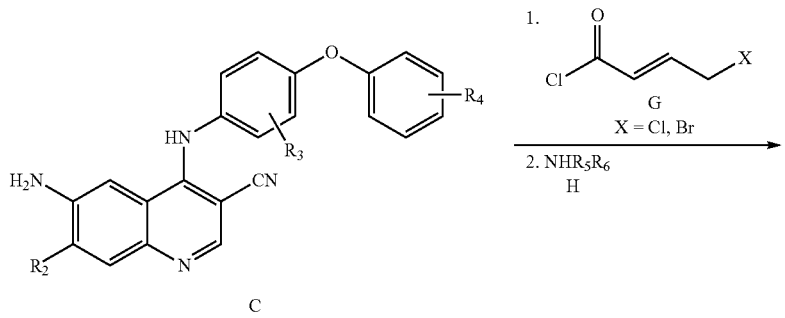

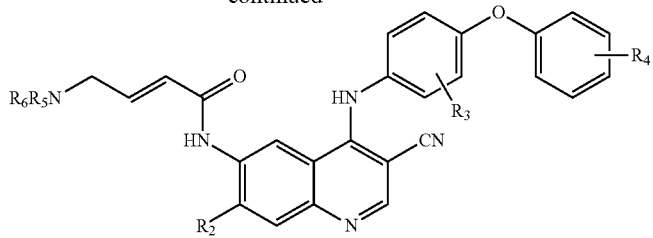

I-1

The synthesis of compounds of I-2 can be conducted by reaction as described in Scheme 4. The reaction of commercial available starting materials 1 with acetic anhydride under heat afforded compound 2. The alkylation of hydroxyl group of compound 2 led to the synthesis of compound 3. The reduction of nitro group first followed by addition/elimination gave compound 4. The cyclization under elevated temperature afforded compound 5. The 4-hydroxyl group in compound 5 was converted into chloride using $POCl_3$ to give compound 6, which reacted with 7 (building block compound B in Scheme 1) to afford 8. The acylation of the amino group of 8 generated the compounds in I-2.

Scheme 4

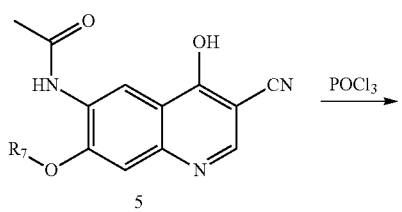

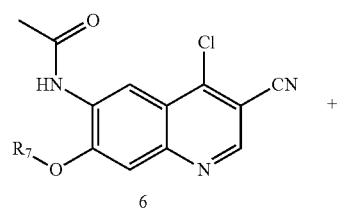

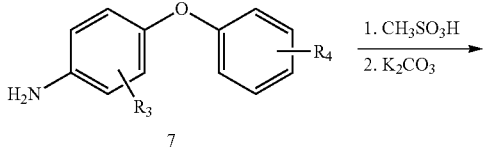

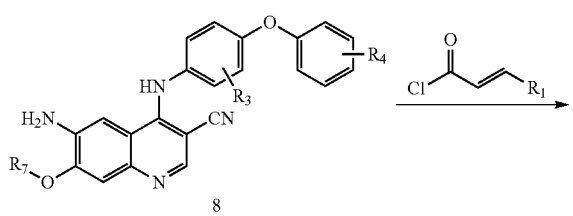

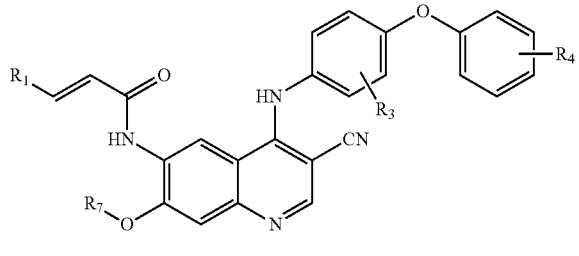

I-2

The synthesis of compound 12 (Example 1) was described in Scheme 5. The reaction between known starting materials compounds 9 and 10 under acidic condition followed by hydrolysis of the amide led to the synthesis of compound 11, which reacted with (E)-4-(dimethylamino)but-2-enoyl chloride to give compound 12 (Example 1).

Scheme 5

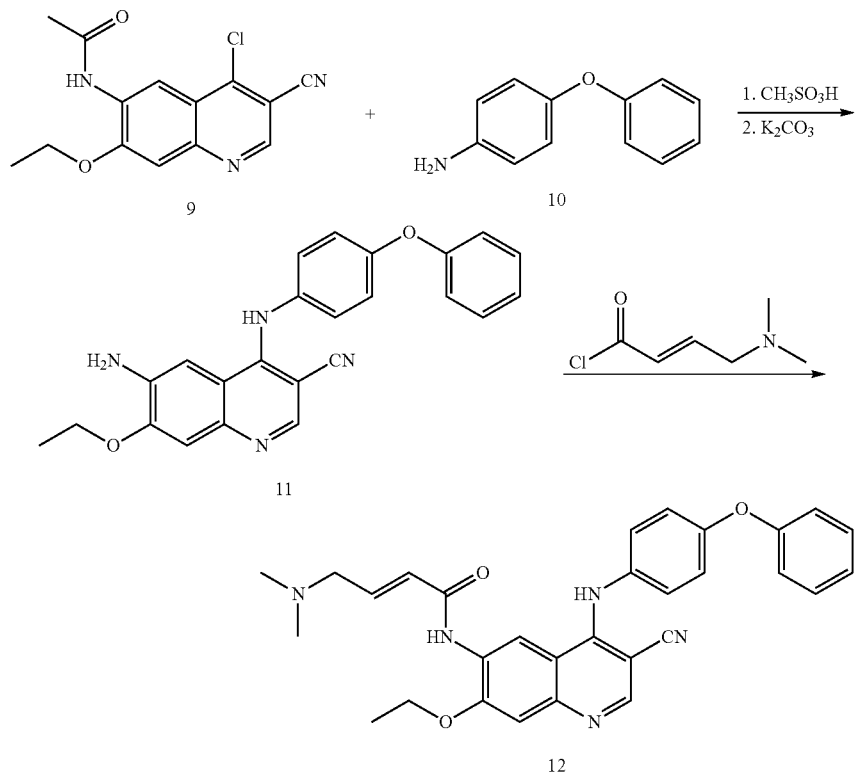

The synthesis of compounds 21 and 22 was described in Scheme 6. The reaction of 13 and 14 in Toluene gave compound 15, which underwent intramolecular cyclization to afford compound 16. Chlorination with POCl₃ to generate compound 17, which reacted with compound 10 to afford 18. The nitro group of 18 was reduced by iron to give compound 19, which reacted with 20 to afford compounds 21 or 22

Scheme 6

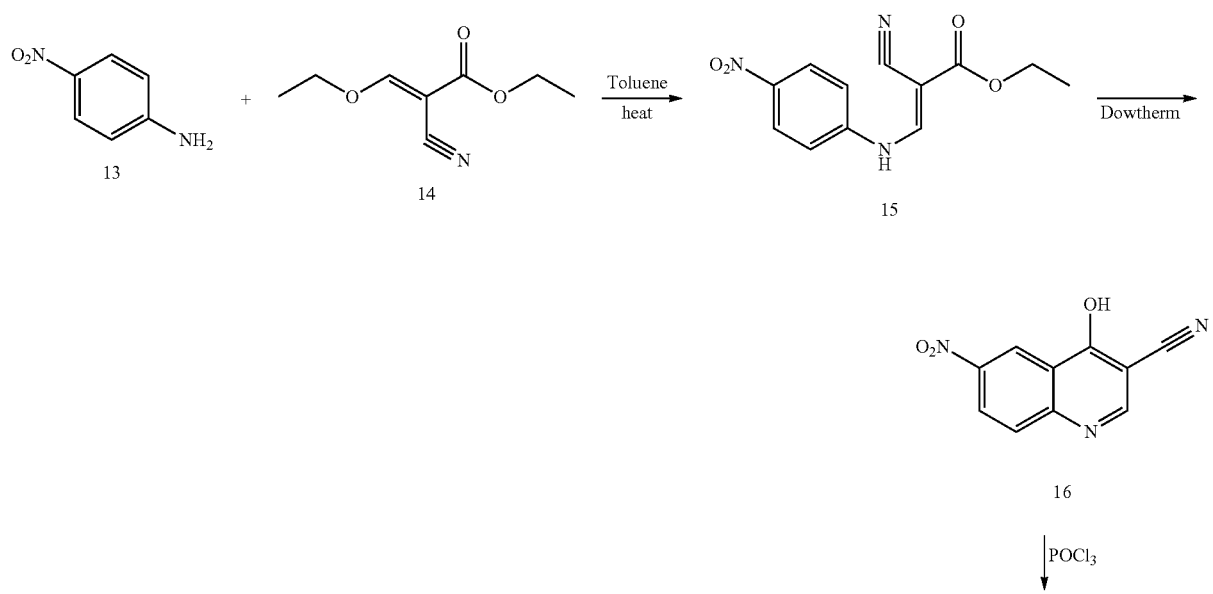

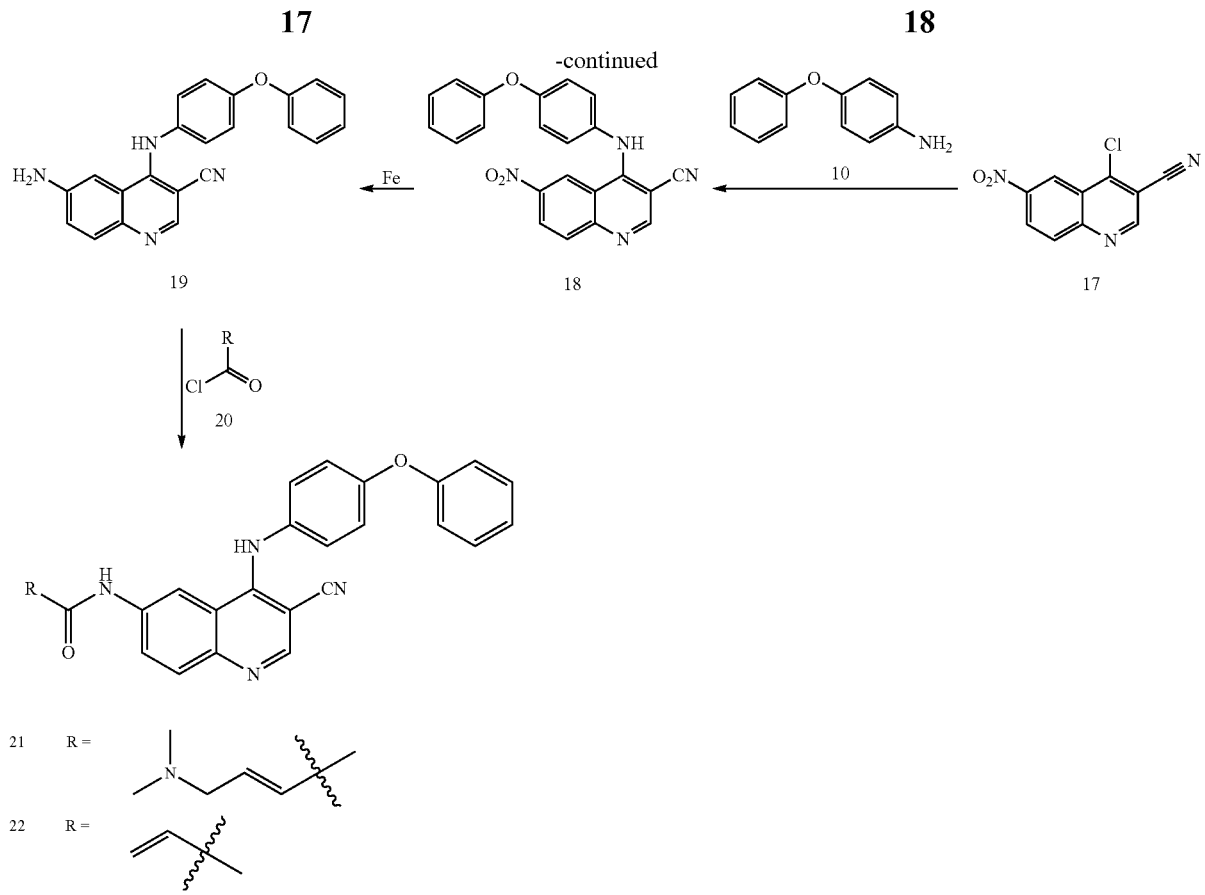

Example 1

Preparation of (E)-N-(3-cyano-7-ethoxy-4-((4-phenoxyphenyl)amino)quinolin-6-yl)-4-(dimethylamino)but-2-enamide (Compound 12)

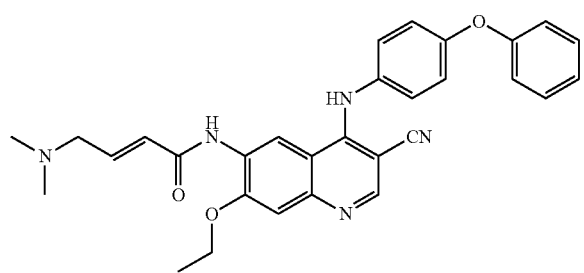 [SMILES: CCOc1cc2ncc(C#N)c(Nc3ccc(Oc4ccccc4)cc3)c2cc1NC(=O)/C=C/CN(C)C]

Step 1: A mixture of 4-chloro-3-cyano-7-ethoxy-6-N-acetylaminoquinoline (11.64 g), 4-phenoxy aniline (9.2 g), methanesulfonic acid (1.3 mL) and ethanol (300 mL) was stirred together and heated to reflux for 6 hours. 0.6 N Hydrogen chloride (600 mL) was added. The mixture was heated at 80° C. for 19 hours, then cooled to 0° C. and the precipitated solids were filtered and added to a solution of 1 N potassium carbonate (200 mL) in methanol (300 mL). The mixture was stirred for 3 hours and the solid was filtered, washed with 1:1 methanol/water (500 mL) and dried to give the desired product 6-amino-7-ethoxy-4-((4-phenoxyphenyl)amino)quinoline-3-carbonitrile (12.8 g).

Step 2: A solution of 4-N,N-dimethyl-aminocrotonic acid hydrochloride (1.28 g) in THF (18 mL) and a catalytic amount of DMF was cooled to 5° C., the oxalyl chloride (0.67 mL) was added dropwise. The mixture was then warmed to room temperature and stirred for 3 hours. A solution of 6-amino-7-ethoxy-4-((4-phenoxyphenyl)amino)quinoline-3-carbonitrile in N-methyl-2-pyrrolidinone (20 ml) was added dropwise over 10 minutes. The reaction mixture was stirred overnight and then quenched with water. Aqueous sodium hydroxide was added slowly to bring the pH to 11. It was stirred for another 1 hour and the resulting precipitate was filtered and washed with water. The wet solid was recrystallized in acetonitrile and THF and dried to give desired product (E)-N-(3-cyano-7-ethoxy-4-((4-phenoxyphenyl)amino)quinolin-6-yl)-4-(dimethylamino)but-2-enamide (1.56 g). $^1$H-NMR (400 MHz, CDCl$_3$, ppm): 9.17 (1H, s), 8.52 (1H, s), 8.10 (1H, s), 7.37-6.97, (13H, m), 6.20 (1H, d, J=15.6 Hz), 4.32 (2H, q, J=7.2 Hz), 3.17-3.15 (2H, m), 2.31 (6H, s), 1.57-1.69 (3H, t, J=7.2 Hz). MS m/z 508.3[M+1].

Example 2

Preparation of (E)-N-(3-cyano-4-((4-phenoxyphenyl)amino)quinolin-6-yl)-4-(dimethylamino)but-2-enamide (Compound 21)

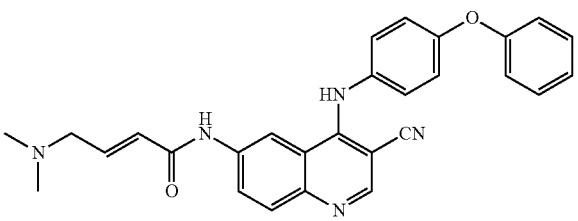 [SMILES: CN(C)C/C=C/C(=O)Nc1ccc2ncc(C#N)c(Nc3ccc(Oc4ccccc4)cc3)c2c1]

Example 2 was prepared as an off-white solid using a procedure that was described in Scheme 6.

Step 1: A mixture of 4-nitroaniline (27.6 g, 200 mmol), ethyl(ethoxymethylene) cyanoacetate (11.33 g, 200 mmol), and 100 mL of toluene was stirred at 100° C. for 1 h and at 125° C. for 15 min. Then toluene was removed under vacuum, the residue was recrystallized from EA (450 mL) to give (E)-ethyl 2-cyano-3-((4-nitrophenyl)amino)acrylate (Compound 15) as a solid (45 g).

Step 2: A mixture of (E)-ethyl 2-cyano-3-((4-nitrophenyl) amino)acrylate (24.0 g) and Dowtherm A (500 mL) was added to a 1 L flask, the mixture was heated to reflux under nitrogen for 10 hours. After cooling to 50° C., the mixture was diluted with hexane (1 L). The product was filtered, washed with ethanol (100×2 mL), and dried to give 4-hydroxy-6-nitroquinoline-3-carbonitrile (Compound 16) as a brown solid (12.0 g).

Step 3: mixture of 4-hydroxy-6-nitroquinoline-3-carbonitrile (11.0 g) and 50 mL of $POCl_3$ was heated at reflux for 7 hours. The volatile materials were removed under vacuum at 70° C. The residue was stirred at 0° C. with methylene chloride and $H_2O$, and solid $K_2CO_3$ was carefully added until the pH was 8-9. After stirring for 30 min at rt, the organic layer was separated, washed with $H_2O$, dried and evaporated under vacuum to give a crude solid. Purification on a silica gel column gave the 4-chloro-6-nitroquinoline-3-carbonitrile (Compound 17) as an off-white solid (4.2 g).

Step 4: A mixture of -chloro-6-nitroquinoline-3-carbonitrile (4.1 g, 17.6 mmol, 1.0 eq), 4-phenoxyaniline (2.6 g, 14.1 mmol, 0.8 eq) was dissolved in ethanol (40 mL). The reaction was heated to reflux for 2 hours, cooled to room temperature, poured into water (50 mL), and washed with ethyl acetate (50×2 mL). It was filtrated and dried in vacuum to give 6-nitro-4-((4-phenoxyphenyl)amino)quinoline-3-carbonitrile (Compound 18) as a solid (5.6 g)

Step 5: Fe (2.9 g, 52.4 mmol, 4.0 eq) and $NH_4Cl$ was added to a solution of 6-nitro-4-((4-phenoxyphenyl)amino)quinoline-3-carbonitrile (5.0 g, 13.1 mmol, 1.0 eq) in methanol/water (50/50 mL). The mixture was heated to reflux for 8 hours, cool to room temperature and extracted with ethyl acetate (100×3 mL). The organic layers were combined, dried over anhydrous sodium sulfate. The crude product was purified by flash column chromatography on silica gel to give 6-amino-4-((4-phenoxyphenyl)amino)quinoline-3-carbonitrile (Compound 19) as a solid 3.5 g.

Step 7: Oxalyl chloride (229 mg, 1.80 mmol, 1.5 eq) was added to a solution of 4-(dimethylamino)-1-ylbut-2-enoicacid hydrochloride (200 mg, 1.2 mmol, 1.0 eq) in THF (4 mL) under ice-water bath. This was followed by the addition of a trace amount of DMF. This solution was stirred at rt for 3 hours before added to a solution of. This solution was then cooled in an ice-water bath, and 6-amino-4-((4-phenoxyphenyl)amino)quinoline-3-carbonitrile (253 mg, 0.72 mmol, 0.6 eq) in N-methylpyrrolidinone (5 mL) was added dropwise. The reaction was allowed warmed to room temperature over 4 hours before poured into saturated aqueous $NaHCO_3$ solution, extracted with EA (3×50 mL). The organic layers were combined, dried over anhydrous sodium sulfate and concentrated under vacuum. The crude product was purified by flash column chromatography in silica gel to give (E)-N-(3-cyano-4-((4-phenoxyphenyl)amino)quinolin-6-yl)-4-(dimethylamino)but-2-enamide (Compound 21) as an off-white solid 39 mg. $^1$H-NMR (300 MHz, DMSO-d6): δ 8.83 p.p.m. (1H, s), 8.56 (1H, s), 7.97 (1H, d, J=6.6 Hz), 7.85 (1H, m), 7.52 (1H, dd, J=6.6, 1.5 Hz), 7.35 (2H, m), 7.12 (1H, m), 7.07 (5H, m), 7.02 (2H, m), 6.22 (1H, d, J=11.7 Hz), 3.19 (3H, m), 2.38 (6H, s).

Example 3

Preparation of N-(3-cyano-4-((4-phenoxyphenyl) amino)quinolin-6-yl)acrylamide (Compound 22)

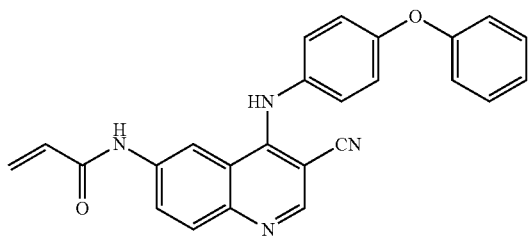 [SMILES: C=CC(=O)Nc1ccc2ncc(C#N)c(Nc3ccc(Oc4ccccc4)cc3)c2c1]

Example 3 was prepared as an off-white solid using a procedure similar to that described for the synthesis of compound 21 (Example 2). Triethylamine (1.03 g, 10.2 mmol, 1.2 eq) and acryloyl chloride (926 mg, 10.2 mmol, 1.2 eq) were added to an ice cold solution of 6-amino-4-((4-phenoxyphenyl)amino)quinoline-3-carbonitrile (3.0 g, 8.5 mmol, 1.0 eq) in THF (50 mL) under nitrogen. The reaction was stirred at rt for 2 hours. The water was added. The water layer was extracted with EA, dried over anhydrous sodium sulfate. The crude product was purified by column chromatography on silica gel to give N-(3-cyano-4-((4-phenoxyphenyl)amino) quinolin-6-yl)acrylamide as an off-white solid 1.2 g.

$^1$H-NMR (300 MHz, DMSO-d6): δ 10.51 p.p.m. (1H, s), 9.82 (1H, s), 8.85 (1H, s), 8.51 (1H, s), 7.89 (2H, m), 7.35 (4H, m), 7.08 (5H, m), 6.52 (1H, m), 6.32 (1H, m), 5.85 (1H, m).

Indication

The present invention provides compounds which are capable of modulating one or more signal transduction pathways comprising, but not limited to Bruton's tyrosine kinases (Btk). By the term "modulate," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating cancer with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc.

Tablets also generally contain lubricants such as magnesium stearate, calcium stearate, zinc stearate, sodium stearyl fumarate, and mixtures of magnesium stearate with sodium lauryl sulphate.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The final formulation may include one or more layers and may be coated or uncoated; or encapsulated. The formulation of tablets is discussed in detail in "*Pharmaceutical Dosage Forms: Tablets, Vol. I*", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, *Pharmaceutical Technology On-line*, 25(2), 1-14 (2001). The use of chewing gum to achieve controlled release is described in WO 00135298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

In some embodiments, methods for treatment of androgen receptor-dependent or androgen receptor-mediated conditions or diseases, such as proliferative disorders, including cancer, comprises administration to a mammal a compound of Formulas I in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

Specifically, the administration of compounds of the present invention in some embodiments are in conjunction with additional therapies known to those skilled in the art in the prevention or treatment of cancer. The foregoing description is merely illustrative of the invention and is not intended to limit the invention to the disclosed compounds, compositions and methods.

What is claimed is:

1. A compound according to Formula I:

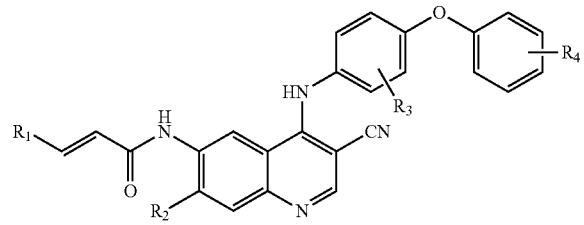

or a pharmaceutically acceptable salt, solvate or a stereoisomer or a tautomer thereof, wherein $R_1$ is selected from
a) Hydrogen or —$(CH_2)_m$—$NR_5R_6$;
b) —$(CH_2)_m$-Het; Het is morpholine, piperidine, piperazine, piperazine-$N(C_1$-$C_3$ alkyl), pyrrolidine, each optionally substituted by alkyl, halo, OH, NH2, NH($C_1$-$C_3$ alkyl) or N($C_1$-$C_3$ alkyl)$_2$;

$R_2$ is selected from
a) Hydrogen, $C_1$-$C_6$ alkyl, F, Cl or $CF_3$;
b) —$OR_7$;

$R_3$ is H, $R_4$ is selected from hydrogen, $C_1$-$C_6$ alkyl, halo, CN, or $CF_3$;

$R_5$ and $R_6$ are independently selected from hydrogen, or $C_1$-$C_6$ alkyl;

$R_7$ is selected from
a) $C_1$-$C_6$ straight or branched alkyl, optionally substituted by one or more halogens or $C_1$-$C_6$ alkoxy;
b) Tetrahydrofuran-3-yl;
c) —$(CH_2)_m$-morpholine, —$(CH_2)_m$-piperidine, —$(CH_2)_m$-piperazine-N($C_1$-$C_3$ alkyl); m is 1-3.

2. The compound of claim 1, wherein $R_1$ is H or —$CH_2N(CH_3)_2$.

3. The compound of claim 1, wherein $R_2$ is H, —$OCH_3$ or —$OCH_2CH_3$.

4. The compound of claim 1, wherein $R_4$ is H, F, Cl, CN or $CF_3$.

5. The compound of claim 1, wherein the compound is selected from the group consisting of:
N-(3-cyano-4-((4-phenoxyphenyl)amino)quinolin-6-yl) acrylamide;
N-(4-((4-(3-chlorophenoxy)phenyl)amino)-3-cyano-quinolin-6-yl)acrylamide;
N-(3-cyano-7-methoxy-4-((4-phenoxyphenyl)amino) quinolin-6-yl)acrylamide;
N-(3-cyano-7-ethoxy-4-((4-phenoxyphenyl)amino) quinolin-6-yl)acrylamide;
N-(3-cyano-7-ethoxy-4-(4-(3-(trifluoromethyl)phenoxy) phenyl)amino)quinolin-6-yl)acrylamide;
N-(3-cyano-4-((4-phenoxyphenyl)amino)-7-((tetrahydrofuran-3-yl)oxy)quinolin-6-yl)acrylamide;
(R)—N-(3-cyano-4-((4-phenoxyphenyl)amino)-7-((tetrahydrofuran-3-yl)oxy)quinolin-6-yl)acrylamide;

N-(3-cyano-4-((4-(3-(trifluoromethyl)phenoxy)phenyl)
amino)quinolin-6-yl)acrylamide;
N-(3-cyano-7-ethoxy-4-((4-(4-fluorophenoxy)phenyl)
amino)quinolin-6-yl)acrylamide;
(E)-N-(3-cyano-7-ethoxy-4-((4-phenoxyphenyl)amino)
quinolin-6-yl)-4-(piperidin-1-yl)but-2-enamide;
(R,E)-N-(3-cyano-4-((4-phenoxyphenyl)amino)-7-((tetrahydrofuran-3-yl)oxy)quinolin-6-yl)-4-(dimethylamino)but-2-enamide;
(E)-N-(3-cyano-7-ethoxy-4-((4-phenoxyphenyl)amino)
quinolin-6-yl)-4-(dimethylamino)but-2-enamide;
(E)-N-(3-cyano-4-((4-phenoxyphenyl)amino)-7-((tetrahydrofuran-3-yl)oxy)quinolin-6-yl)-4-(dimethylamino)but-2-enamide;
(E)-N-(3-cyano-4-((4-phenoxyphenyl)amino)quinolin-6-yl)-4-(piperidin-1-yl)but-2-enamide;
(E)-N-(3-cyano-4-((4-phenoxyphenyl)amino)quinolin-6-yl)-4-(dimethylamino)but-2-enamide; and
(E)-N-(3-cyano-7-ethoxy-4-((4-(4-fluorophenoxy)phenyl)amino)quinolin-6-yl)-4-(dimethylamino)but-2-enamide.

6. A pharmaceutical composition comprising a compound of claim 1 and a pharmaceutically acceptable carrier.

7. A method of inhibiting Btk, the method comprising a step of administering to the subject an effective amount of a pharmaceutical composition comprising a compound of claim 1 and a pharmaceutically acceptable carrier.

8. The method of claim 7, further comprising a step of co-administering to the subject with one or more anti-cancer agents, wherein the first disease or condition is neoplasia.

* * * * *